United States Patent [19]

Assenza et al.

[11] 4,248,234
[45] Feb. 3, 1981

[54] CATHETER WITH VARIABLE FLEXURAL MODULUS AND METHOD OF USING SAME

[75] Inventors: John S. Assenza, Basking Ridge; Joseph J. Thomas, Bridgewater, both of N.J.

[73] Assignee: Critikon, Inc., Tampa, Fla.

[21] Appl. No.: 18,493

[22] Filed: Mar. 8, 1979

[51] Int. Cl.³ .............................................. A61M 25/00
[52] U.S. Cl. .................................... 128/348; 128/344
[58] Field of Search ................ 128/214 R, 214.4, 221, 128/347–350, DIG. 9, DIG. 16, 344

[56] References Cited

U.S. PATENT DOCUMENTS

| | | | |
|---|---|---|---|
| 2,548,602 | 4/1951 | Greenburg | 128/349 B |
| 3,438,375 | 4/1969 | Ericson | 128/349B |
| 3,605,749 | 9/1971 | Heimlich | 128/349 B |
| 3,773,034 | 11/1973 | Burns et al. | 128/DIG. 9 |

*Primary Examiner*—Robert W. Michell
*Assistant Examiner*—C. F. Rosenbaum
*Attorney, Agent, or Firm*—Donal B. Tobin

[57] ABSTRACT

A catheter or like instrument having a variable flexural modulus for insertion into the body includes a length of flexible tubing having a normally relatively low flexural modulus. A first lumen inside the tubing provides a free flow path therethrough. Associated with the catheter tubing for controllably increasing its flexural modulus is a second lumen having a closed distal end and a proximal end adapted to be connected to a pressure source. An increase in pressure inside the second lumen serves to increase the flexural modulus of the catheter tubing to stiffen the same particularly during insertion of the tubing into the body. After insertion of the same, the pressure is controllable so that the catheter tubing is allowed to return to its normally low flexural modulus.

A method of inserting an instrument substantially as described above comprises the steps of increasing the flexural modulus of the catheter tubing prior to insertion into the body, inserting the stiffened tubing into the body and then decreasing the flexural modulus so that the tubing returns to its normally relatively low flexural modulus after the tubing is in position in the body.

3 Claims, 7 Drawing Figures

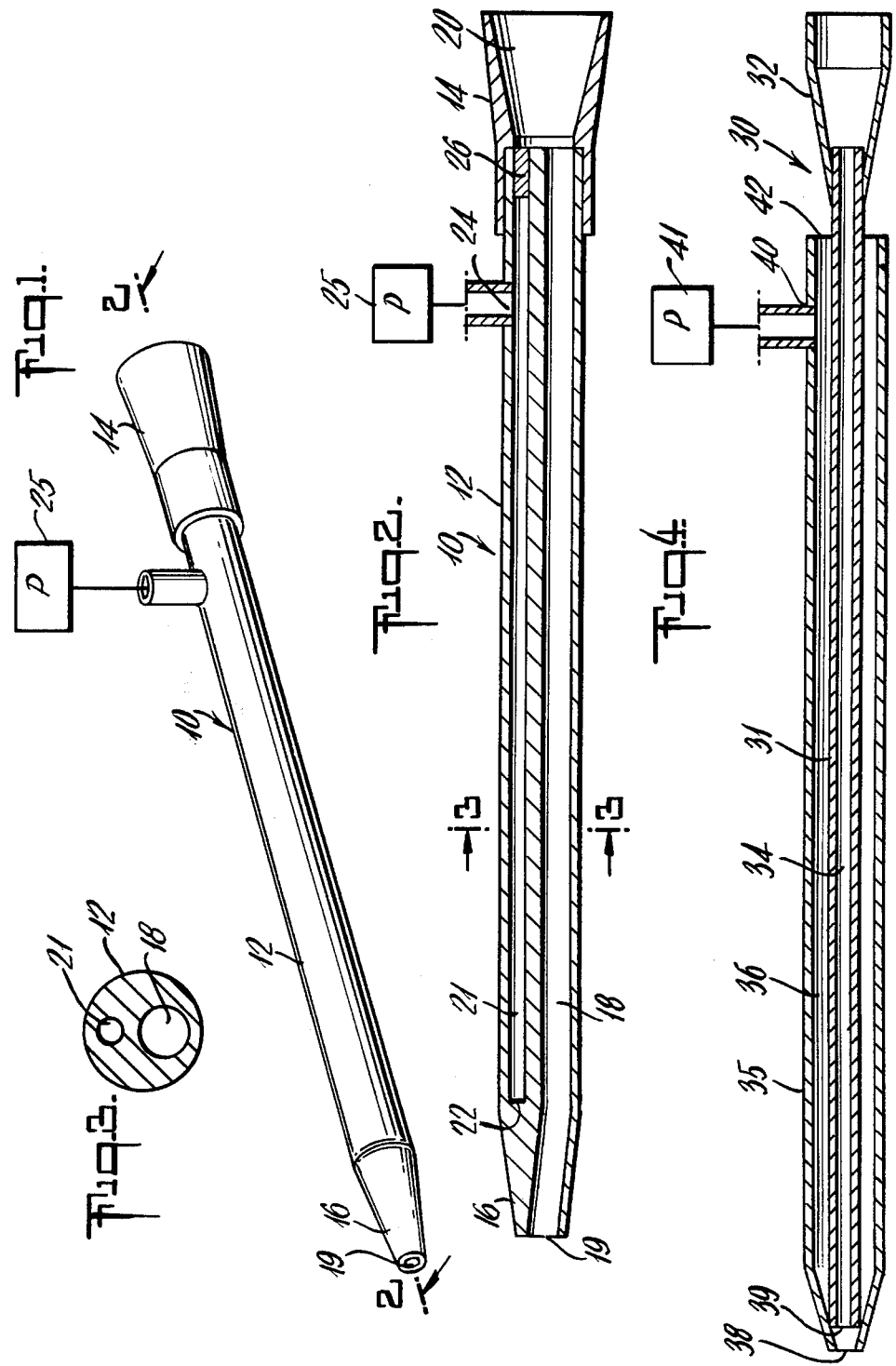

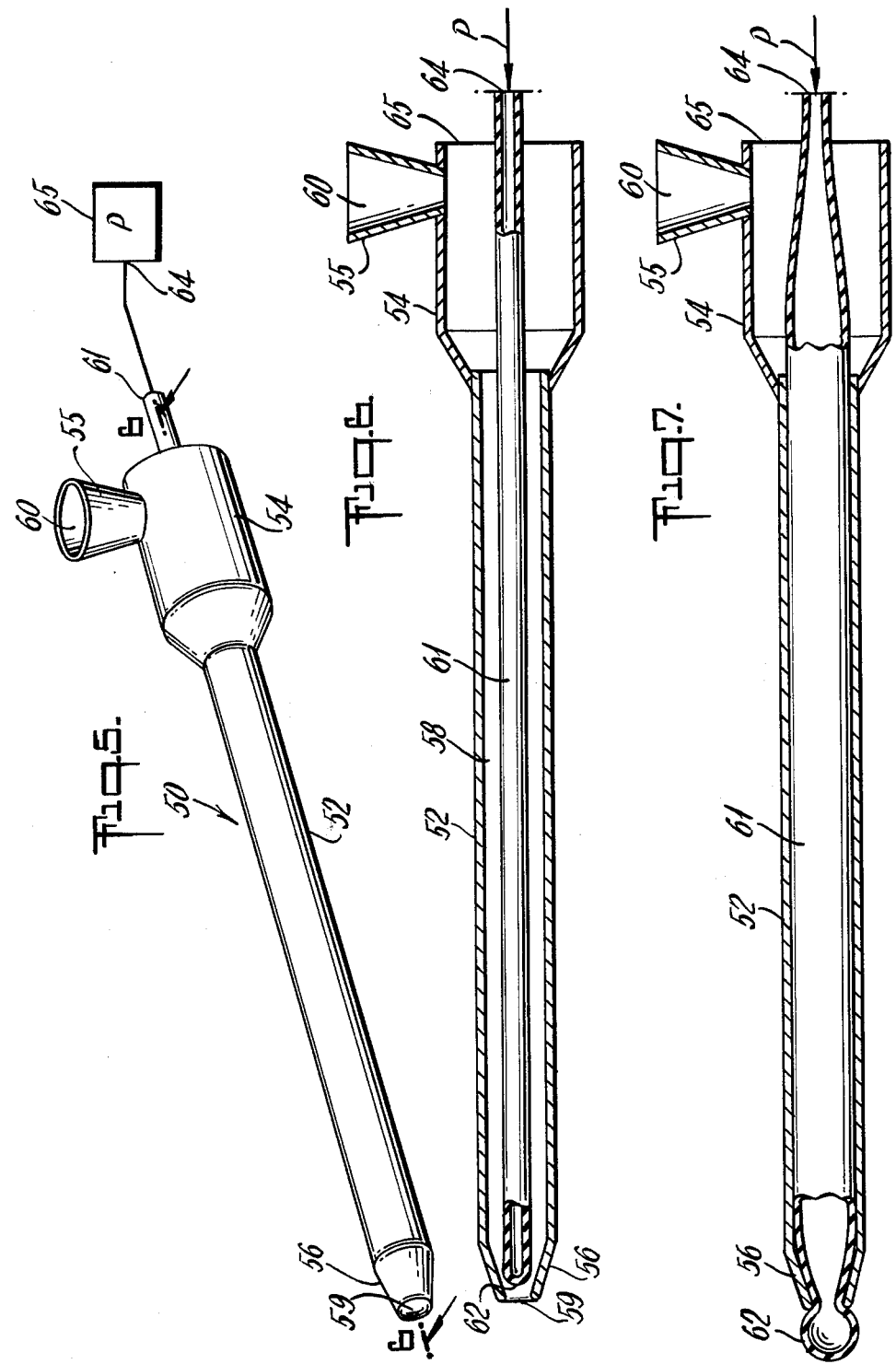

CATHETER WITH VARIABLE FLEXURAL MODULUS AND METHOD OF USING SAME

BACKGROUND OF THE INVENTION

The present invention relates to an instrument for insertion into an animal body, and, more particularly, concerns a catheter or probe for placement into various body orifices, and also concerns a method of inserting such an instrument into an animal body.

Medical instruments, intravascular catheters and the like probes are placed into various body orifices for many purposes, including the infusion of fluids, withdrawal of fluid samples from the body, and for the transduction of other parameters such as pressure, temperature and sound. Very often, such an instrument has to be placed in a remote part of the body or perhaps threaded for a considerable distance in the vascular system. Most catheters of the type for placement, particularly into a deep body position, are made of a pliable, very flexible, plastic material. This facilitates any bending or curving that is necessary during placement and also serves to eliminate or decrease the traumatic effect of its insertion. However, the relatively low flexural modulus of most catheters which provides the pliable nature of the catheter, produces at least one drawback.

A problem arises using most of the very flexible catheters during insertion of the same into the patient. The tendency of the catheter tubing to readily bend and flex during the insertion stage oftentimes produces awkward and erratic threading of the catheter by the operator. This is especially problematical when the catheter is long and is intended to be positioned deep in the patient.

Although some probe-like medical instruments have employed pressurization for various purposes, the variability of the flexural modulus to provide stiffness during insertion and then flexibility thereafter has not been disclosed. For instance, U.S. Pat. No. 3,525,329 discloses an evertable, extensible probe which admits pressure thereinto to extend the probe into the body cavity to be examined. Along the same lines, U.S. Pat. No. 3,502,069 employs a rigid tubular casing and a flexible evertable tubing inside. When fluid pressure is admitted into the casing the tubing is everted out of an open end of the casing. U.S. Pat. No. 3,168,092 describes a probing instrument with a tubing which becomes extraverted under pressure whereby the tubing exerts pressure on the walls of the cavity to separate the walls thereof.

Accordingly, it is most desirable to employ a catheter or like instrument which has a certain level of stiffness or increased flexural modulus of elasticity in order to facilitate placement of the catheter with relative ease into the patient. However, as pointed out above, after placement of the catheter into the final position the stiffness of the same is undesirable since more pliability and flexibility is required. It can be seen, then, that it is desirable to be able to vary the degree of stiffness of catheter tubing so as to have a relatively high degree of stiffness during placement of the catheter into the patient and then a relatively low degree of stiffness after final positioning. It is to this end that the present invention is directed.

SUMMARY OF THE INVENTION

An instrument having a variable flexural modulus for insertion into an animal body comprises a length of flexible tubing having a normally relatively low flexural modulus. A lumen inside the tubing provides a free flow path therethrough. Means is associated with the tubing for controllably increasing the flexural modulus of the tubing to stiffen the same during insertion of the tubing into the body. After being positioned in the body, the means is adapted to allow the tubing to return to its normally relatively low flexural modulus.

In the preferred embodiment of this aspect of the invention, the means for increasing the flexural modulus of the tubing includes a second lumen associated with the catheter tubing. This second lumen has a closed distal end and a proximal end adapted to be connected to a pressure source. An increase in pressure in the second lumen serves to increase the flexural modulus of the catheter tubing, with the pressure being controllable so that the flexural modulus of the catheter is also controllable. This second lumen may be a second tubing located inside the catheter tubing, and, in one embodiment, is removable from the catheter tubing whereby after the catheter is positioned in the body, the second tubing may be removable to completely free the fluid path in the lumen.

Another aspect of the present invention includes a method of inserting an instrument substantially as described above into an animal body. The steps of the method include increasing the flexural modulus of the catheter tubing prior to insertion of the same into the body. The stiffened tubing is then inserted into the body. After the tubing is in position in the body the method includes decreasing the flexural modulus so that the tubing returns to its normally relatively low flexural modulus.

In accordance with the principles of the present invention, the catheter advantageously offers the desirable stiffness characteristic during the placement or insertion stage into the body, while also providing the ability to reduce the stiffness after final positioning so that the catheter may be pliant and flexible. Accordingly, the catheter or like instrument of the present invention allows the operator to manipulate the catheter into the patient with relative ease and substantially eliminates or reduces the awkwardness which accompanies the insertion of catheters which do not have the variable stiffness feature.

BRIEF DESCRIPTION OF THE DRAWINGS

FIG. 1 is a perspective view illustrating the preferred catheter of the present invention;

FIG. 2 is a cross-sectional view taken along line 2—2 of FIG. 1;

FIG. 3 is a cross-sectional view taken along line 3—3 of FIG. 2;

FIG. 4 is a cross-sectional view of an alternative of the embodiment illustrated in FIGS. 1-3;

FIG. 5 is a perspective view illustrating another embodiment of a catheter utilizing the general principles of the present invention;

FIG. 6 is a cross-sectional view taken along line 6—6 of FIG. 5; and

FIG. 7 is a cross-sectional view similar to that of FIG. 6 illustrating the catheter in its increased condition of flexural modulus.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a catheter 10 for insertion into a body orifice, particularly suitable for infusing fluids, withdrawing fluid samples from the body or for the transduction of other parameters such as pressure, temperature and sound. Catheter 10 includes an elongate slender length of catheter tubing 12 which is preferably made of plastic and has a normally relatively low flexural modulus. This imparts a high degree of flexibility and pliability with a concomitantly low degree of stiffness. As pointed out above, this flexibility feature is desirable especially when catheter tubing 12 is very long, so that the tubing may be able to bend and curve into the body orifice and be finally positioned where intended. At the proximal end of tubing 12 it is connected to a hub 14, such as a female Luer connector, for attachment to the monitoring or feeding source.

As seen more clearly by referring to FIGS. 2 and 3, in conjunction with FIG. 1, catheter tubing 12 is a thinwalled tubing having its distal end 16 tapered inwardly in order to facilitate the insertion of this end into the body. Catheter tubing 12 is hollow along its longitudinal dimension thereby providing a first lumen 18 inside which provides a free path for the flow of fluids or other measurement parameters through the tubing. To this end, distal end 16 includes a hole 19 communicating with first lumen 18 in order to keep that end of the first lumen open. At the other end of tubing 12, hub 14 has a passageway 20 therein which communicates with first lumen 18. Thus the fluid path is open between hole 19 in the distal end of the tubing through first lumen 18 and out passageway 20, or vice versa if fluid flows the opposite direction. Located inside catheter tubing 12 substantially along its entire length and substantially parallel to the first lumen is a second lumen 21. In the embodiment being described, second tubing 21 has a closed distal end 22 while its proximal end 24 is connected to a pressure source 25. Thus, first lumen 18 and second lumen 21 are two separated passageways, the former being completely open for the free passage of fluids, the latter being closed and admitting air or other fluids therein from a source in order to stiffen the flexural modulus of the tubing. This operation will be described hereinafter. To assure that second lumen is adequately closed at both ends, a seal plug 26 may be fit into the proximal end of second lumen if that end would normally have been open as a result of the fabrication of the catheter tubing.

Instead of employing two separate lumens, one for pressurization, two separate tubings may also be used, such as the concentric configuration as illustrated in FIG. 4.

In this alternate embodiment, catheter 30 includes catheter tubing 31 and a hub 32 connected to catheter tubing 31. Hub 32 may be a standard female tapered Luer connector. Catheter tubing 31, similar to the above-described embodiment, has a normally relatively low flexural modulus so as to be very flexible and pliant. The catheter tubing is hollow and includes a lumen 34 therethrough to provide a free path for fluid flow. Surrounding catheter tubing 31 is a second tubing 35; an annular clearance space 36 is provided between the inside wall of second tubing 35 and catheter tubing 31. The distal end 38 of the second tubing is tapered in point-like fashion in order to facilitate insertion of the catheter into the patient. At distal end 38 a seal is made with the distal end 39 of catheter tubing 31 so that annular space 36 is closed at the respective distal ends of the tubings. Thus, fluid to or from the body is only allowed to pass through lumen 34 inside the catheter tubing. At the proximal end of second tubing 25 a connection 40 is provided to pressure source 41. Since, in the embodiment being described, connection 40 is provided at a right angle, the rear portion 42 of the catheter is appropriately closed to effectively contain the inflow of the pressurized medium. It can be seen that the pressure of annular space 36 is increased by the pressure flowing in from pressure source 41 with the result that the flexural modulus of catheter tubing 31 is increased. This stiffens the catheter during the insertion and placement stage. After final positioning, the pressure is reduced whereby the normally relatively low flexural modulus of the catheter tubing remains with its normal flexibility. It is appreciated that second tubing 35 surrounding catheter tubing 31 is also flexible and pliant in its normal, relaxed condition so as to be compatible with the catheter tubing.

In operation, and returning to the preferred embodiment of FIGS. 1 to 3, the pressure source is appropriately connected to second lumen 21 prior to insertion of the catheter into the patient. The flexural modulus of the catheter tubing is increased at this time by increasing the pressure inside second lumen 21. A noticeable stiffening effect is observed and felt by the operator of this catheter. In the stiffened condition, the catheter tubing is inserted into the boby of the patient and placed or threaded into the appropriate position. When this step is completed, the pressure source is controlled to de-pressurize the atmosphere inside second lumen 21. In turn, this causes a decrease in the flexural modulus of the catheter tubing so that it then returns to its normally relatively low flexural modulus. Following this step, the appropriate attachment may be made to utilize this catheter for its intended purpose.

Another embodiment of the present invention utilizing the same general principles as the previous embodiments is illustrated in FIGS. 5-7. Catheter 50 includes an elongate slender catheter tubing 52 which normally has a relatively low flexural modulus. Catheter tubing 52 is preferably thin-walled with its distal end 56 tapered inwardly to facilitate insertion of this end into the body. This tubing is hollow along its longitudinal dimension thereby providing a lumen 58 inside which provides a free path for the flow of fluids or the like. A hole 59 in the distal end communicates with lumen 58 to keep that end of the tubing open. At the proximal end of tubing 52, a hub 54 is provided, including a connector 55 thereon. A passageway 60 in the connector communicates with lumen 58. Positioned inside catheter tubing 52 substantially along its entire length is a second tubing 61. This second tubing has a closed end 62 while is proximal end 64 is adapted to be connected to a pressure source 65. As seen particularly in FIGS. 6 and 7, both catheter tubing 52 and second tubing 61 are in the normally relaxed condition; catheter tubing 52 is normally relatively flexible with a low flexural modulus, and second tubing 61 is positioned in lumen 58 so that its distal end 62 faces the insertion end of catheter tubing 52. It is noted that there is an annular clearance between second tubing 61 and the inside wall of catheter tubing 52 so that, if second tubing 61 is to remain permanently in the catheter, the fluid is free to pass through the lumen through the path previously described. It should be pointed out that if second tubing 61 is to remain in the catheter during fluid flow, the rear portion 65 of hub 54 should be appropriately closed so that fluid may effectively flow out of passage 60 in connector 55 rather than out the rear portion in the embodiment being described. Of course, various hub and connection arrangements may be designed which are within the purview of the intended function of the present invention, and which may vary from the particular version illustrated and described.

Turning now to FIG. 7, second tubing 21 is preferably expandable under pressure so that when the same is pressurized it provides a snug fit against the inside wall of catheter tubing 52. At the same time, distal end 62 of the second tubing protrudes slightly out of the insertion end 56 of the catheter tubing; by virtue of its radial expansion, distal end 62 covers the corners of the distal tip of the catheter tubing rendering a relatively smooth tip, free of sharp corners, which will further aid in threading of the catheter and reduce the risk of blood vessel wall or body orifice wall irritation. The pressure to be delivered from pressure source 65 may be either liquids or gases in order to increase the pressure inside second tubing 61. While this increased pressure is maintained, it can be appreciated that the flexural modulus of catheter tubing 52 is increased with the result that the catheter tubing has a higher level of stiffness. This, in turn, provides improved manipulation of the catheter tubing during the placement stage into the body. Once the final, desired position is reached, the controllable pressure from pressure source 65 is reduced thereby returning second tubing 61 to its unexpanded state as that of FIG. 6, while also returning catheter tubing 52 to its normally relatively low flexural modulus. At this time, a suitable connection may be made to connector 55 in order to utilize this catheter for its intended purpose.

While the embodiments of FIGS. 5 to 7 are concerned with a catheter in which second tubing 61 is permanently positioned therein, a slight modification of this embodiment will allow second tubing 61 to be removed after final positioning. In this modification, rear portion 65 of hub 54 is not necessary since second tubing 61 will merely lie inside lumen 58 during the placement and pressurization periods. Thereafter, second tubing 61 is removable from the inside of catheter tubing 52 thereby completely freeing the fluid path in lumen 58. In this modification, connector 55 may also be eliminated, hub 54 serving as the connection medium to which the appropriate device is to be connected. Hub 54, in this instance, may typically be a standard female Luer connector.

Thus, a medical instrument for insertion into an animal body has been provided with a variable flexural modulus to stiffen the same during insertion and placement into the body, and to relax and render pliable and flexible the catheter after the same has been finally positioned.

We claim:

1. A catheter having a variable flexural modulus for insertion into a human body comprising:
   a length of catheter tubing having a normally relatively low flexural modulus, said tubing having a first lumen for providing a free path for the flow of fluid through said tubing;
   a second tubing located within said catheter tubing and defining a second lumen having a closed distal end and a proximal end adapted to be connected to a pressure source;
   said second tubing lying in said path for flow of fluid with its distal end facing the insertion end of said catheter tubing, and, in its normal condition, said second tubing providing a clearance between itself and the inside wall of said catheter tubing so that fluid is free to pass through said lumen, said second tubing being expandable under pressure to provide a snug fit against the inside wall of said catheter tubing when pressurized to thereby increase the flexural modulus of said catheter tubing;
   said second tubing being removable from said catheter tubing;
   whereby after said catheter is positioned in said body the second tubing may be removed to completely free the fluid path in said lumen.

2. A catheter as defined in claim 1 wherein the distal end of said second tubing is adapted to protrude slightly out of the insertion end of said catheter tubing when pressurized to thereby provide a smooth tip for said catheter upon its insertion into the human body.

3. A catheter having a variable flexural modulus for insertion into a human body comprising:
   a length of catheter tubing having a normally relatively low flexural modulus, said tubing having a first lumen for providing a free path for the flow of fluid through said tubing;
   a second tubing associated with said catheter tubing and defining a second lumen;
   said second lumen having a closed distal end and a proximal end adapted to be connected to a pressure source, whereby a change in pressure in said second lumen serves to change the flexural modulus of said catheter tubing; and,
   said second tubing being removably associated with said catheter tubing, whereby after said catheter is positioned in said body, the second tubing may be removed to completely free the fluid path in said lumen.

* * * * *